(12) United States Patent
Frampton et al.

(10) Patent No.: US 8,454,944 B2
(45) Date of Patent: Jun. 4, 2013

(54) RE-APPLICABLE MASCARA COMPOSITION

(75) Inventors: Katie Ann Frampton, West Bablyon, NY (US); Paul Henry Marotta, Farmingdale, NY (US); John R. Castro, Huntington Station, NY (US); Arlene G. Ting-Jenulis, East Northport, NY (US)

(73) Assignee: ELC Management, LLC, New York, NY (US)

( * ) Notice: Subject to any disclaimer, the term of this patent is extended or adjusted under 35 U.S.C. 154(b) by 584 days.

(21) Appl. No.: 12/486,553

(22) Filed: Jun. 17, 2009

(65) Prior Publication Data
US 2010/0028285 A1 Feb. 4, 2010

Related U.S. Application Data

(60) Provisional application No. 61/076,825, filed on Jun. 30, 2008.

(51) Int. Cl.
*A61Q 1/10* (2006.01)
*A61K 8/92* (2006.01)
*A61K 8/41* (2006.01)
*A61K 8/42* (2006.01)
*A61K 8/81* (2006.01)

(52) U.S. Cl.
USPC .................. 424/70.7; 424/70.15; 424/70.16; 424/70.17; 514/579

(58) Field of Classification Search
USPC ............................ 424/400, 70, 70.7; 514/579
See application file for complete search history.

(56) References Cited

U.S. PATENT DOCUMENTS

| 4,980,155 | A | * | 12/1990 | Shah et al. ...................... 424/63 |
| 5,684,105 | A | | 11/1997 | Zhong et al. |
| 5,750,121 | A | | 5/1998 | Rokitowski |
| 6,464,967 | B1 | | 10/2002 | Collin |
| 6,726,917 | B2 | | 4/2004 | Kanji et al. |
| 2003/0026815 | A1 | | 2/2003 | Scott et al. |
| 2005/0025736 | A1 | | 2/2005 | Jachowicz et al. |
| 2005/0061349 | A1 | * | 3/2005 | Patel et al. ..................... 132/218 |
| 2005/0281774 | A1 | | 12/2005 | Muller et al. |
| 2007/0212316 | A1 | * | 9/2007 | Feng et al. .................... 424/70.7 |
| 2009/0202465 | A1 | * | 8/2009 | Mougin et al. ............. 424/70.15 |

FOREIGN PATENT DOCUMENTS
WO WO00/68282 11/2000

OTHER PUBLICATIONS

Kaboodle.com [Downloaded Sep. 6, 2011] [Retrieved from internet URL: http://shine.yahoo.com/channel/beauty/5-surprising-and-handy-uses-for-mascara-1243999 >] (4 pages).*
Styleeze® CC-10 (Ashland [Downloaded Jan. 3, 2012] [Retrieved from internet <URL: http://online1.ispcorp.com/en-US/Pages/ProductDetail.aspx?BU=Performance%20Chemicals &ll=Adhesives&prodName=Styleze%C2%AE%20CC-10 &prdId=72244 >]), 3 pages.*
Styleeze® CC-10 Product Specification (International Specialty Products (ISP) [Downloaded Jan. 3, 2012] [Retrieved from internet <URL: http://online1.ispcorp.com/Specs/11_STYLEZE%20CC-10.pdf >], product specification dated Aug. 4, 2008), 2 pages.*
PCT International Search Report; International Application No. PCT/US2009/047796; Completion Date: Jan. 20, 2010; Date of Mailing: Feb. 1, 2010.
PCT Written Opinion of the International Searching Authority, Or the Declaration; International Application No. PCT/US2009/047796; Completion Date: Jan. 20, 2010; Mailing Date: Feb. 1, 2010.

* cited by examiner

*Primary Examiner* — Jason M Sims
*Assistant Examiner* — Miriam A Levin
(74) *Attorney, Agent, or Firm* — Cynthia R. Miller

(57) ABSTRACT

The present invention relates to a re-applicable mascara composition containing a unique combination of a chemically modified wax and a polymeric film former including a copolymer of vinylpyrrolidone and aminoacrylates. The mascara composition of the present invention can be readily re-applied to eyelashes hours after the initial application to increase the lash volume, without the discomfort and clumping commonly caused by attempts to re-apply mascara to already-coated eyelashes.

21 Claims, No Drawings

RE-APPLICABLE MASCARA COMPOSITION

CROSS-REFERENCE TO RELATED APPLICATIONS

This claims priority to U.S. Provisional Patent Application No. 61/076,825 filed on Jun. 30, 2008.

FIELD OF THE INVENTION

The present invention relates to a cosmetic composition suitable for application to keratinous fibers, more preferably to eyelashes. The cosmetic composition of the present invention contains a unique combination of a chemically modified wax and a polymeric film-former, which provides excellent re-wettability and allows re-application of the cosmetic composition to the eyelashes for boosting the lash volume hours after the initial application without having to remove the initial coating from the eyelashes.

BACKGROUND OF THE INVENTION

Traditional mascaras are made of various film formers dispersed in one or more solvents. After application, the solvents evaporate and leave a rigid, liquid-impervious coating composed of the film formers on the eyelashes. Such coating is designed to adhere securely to the eyelashes and stays thereon for an extended period of time to achieve the desired long wear effect. However, such rigid, liquid-impervious coating, once formed, cannot be re-wetted by the mascara composition, which renders it very difficult to apply additional coatings to the eyelashes to freshen up the previously applied mascara or to boost the lash volume.

There is notable discomfort when a user tries to brush through mascara-covered eyelashes. Separation of eyelashes becomes extremely difficult, with significant clumping as well as potential flaking of the initial coating. Currently there is no commercially available mascara composition that allows comfortable re-application of the mascara over a previously applied, already-dried mascara coating for achieving a more dramatic effect. Therefore, in order to boost the lash volume and achieve the desired dramatic effect, the user typically has to completely remove the previously applied mascara coating and all other eye makeup before re-applying a more volumizing mascara product.

There is therefore a need for a new mascara composition that allows comfortable re-application over mascara-coated eyelashes. It will be especially advantageous to provide a mascara composition that enables the user to achieve a modest daytime look with just one initial coating of mascara, and then re-apply as many additional coatings as needed to continuously build up the lash volume to achieve a more dramatic evening look, without having to remove the initial coating of mascara and with minimum discomfort and clumping. It is also desired to provide a low smudge or zero smudge mascara composition that does not interact with the sebum of the skin and can therefore be worn by the user with comfort comparable to that of the conventional mascara products.

SUMMARY OF THE INVENTION

The present invention relates in general to a mascara composition with sufficient re-wettability suitable for re-application.

In one aspect, the present invention relates to a mascara composition containing:

(a) a chemically modified wax with one or more hydrophilic functional groups;
(b) a polymeric film former comprising monomers having the formula

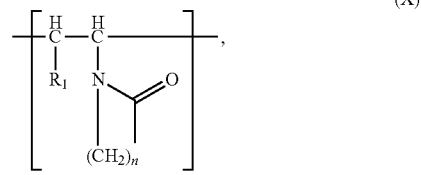

and monomers having the formula

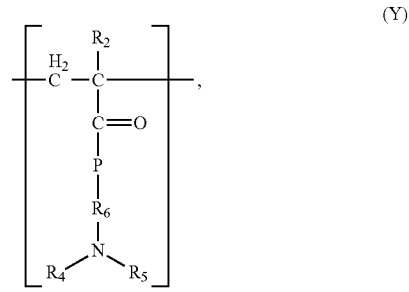

wherein n is 3 to 6; P is O or $NR_3$; $R_1$, $R_2$, $R_3$, $R_4$, and $R_5$ are independently H or $C_1$-$C_5$ alkyl; R6 is $C_2$-$C_{16}$ alkyl or alkylene; wt % of X monomers ranges from about 60 to about 99; and wt % of Y monomers ranges from about 1 to about 40;

(c) pigments; and
(d) water.

In another aspect, the present invention relates to a method of enhancing the appearance of eyelashes, including applying a first coating of the above-described mascara composition over the eyelashes, and subsequently applying one or more additional coatings of such mascara composition over the eyelashes after the first coating is allowed to dry thereon for a sufficient period of time.

Other aspects and objectives of the present invention will become more apparent from the ensuing description, examples, and claims.

DETAILED DESCRIPTION OF THE INVENTION AND PREFERRED EMBODIMENTS THEREOF

Except in operating and comparative examples, or where otherwise explicitly indicated, all numbers in this description indicating amounts or ratios of material or conditions of reaction, physical properties of materials and/or use are to be understood as modified by the word "about." All percentages are presented as percentages by weight of the final composition, unless otherwise specified.

The present invention employs a unique combination of a chemically modified wax and a particular polymeric film former to form a mascara composition with excellent re-wettability that can be readily re-applied to eyelashes already coated with such mascara. The mascara composition of the present invention can be used for freshening up the initial look after an extended period of time, or it can be used to provide as many additional coatings as needed to continuously build up the lash volume so as to achieve a more dramatic effect.

The mascara composition is an aqueous-based composition. The term "aqueous-based" as used herein broadly covers any composition containing one or more aqueous phases, including, but not limited to: compositions containing primarily aqueous phase, oil-in-water (O/W), water-in-oil (W/O), oil-in-water-in-oil (O/W/O) or water-in-oil-in-water (W/O/W) emulsions containing both oil and aqueous phases, water-in-silicone or silicone-in-water emulsions, and the like. Preferably, the mascara composition of the present invention is in the form of an oil-in-water emulsion. The aqueous phase(s) can be present in the mascara composition of the present invention in a total amount ranging from about 1% to about 90%. More preferably, the aqueous phase(s) is present at a large amount in the mascara composition of the present invention, e.g., more than 20%, and most preferably from about 40% to about 70%, by total weight of the composition.

The term "chemically modified wax" means a natural or synthetic wax that has been functionalized with hydrophilic functional groups. Preferably, but not necessarily, the chemical modified wax of the present invention is formed by reacting a natural or synthetic wax having carboxylic acid groups with a mono-, di-, or polyhydric alcohol or alkoxylated alcohol, a $C_2$-$C_4$ alkylene glycol and the like. More preferably, the chemical modified wax of the present invention is a natural wax having carboxylic acid groups reacted with an ethoxylated alcohol, preferably polyethylene glycol (PEG). Exemplary waxes suitable for use in the present invention include natural or synthetic waxes reacted with polyethylene glycol, where the number of repeating ethylene oxide groups ranges from about 2 to 100. Such waxes include, but are not limited to: PEG-esterified beeswax, PEG-esterified candelilla wax, PEG-esterified carnauba wax, PEG-esterified lanolin, PEG-esterified spermaceti wax, PEG-esterified shellac wax, PEG-esterified bayberry wax, and PEG-esterified sugar cane wax, among which PEG-8 beeswax, PEG-6 beeswax, PEG-12 beeswax, PEG-12 carnauba wax, and PEG-sorbitan beeswax are preferred. Most preferred is PEG-8 beeswax, which is commercially available under the trade name "APIFIL®" from Gattefossé Canada Inc. in Toronto, Canada.

The chemically modified wax can be pre-formed by first reacting the above-described natural or synthetic wax with the alcohol at an elevated temperature and then mixed with other ingredients to form the compositions of the present invention. Alternatively, the chemically modified wax can be formed in situ, e.g., by mixing the above-described natural or synthetic wax and the alcohol with other ingredients of the composition of the present invention and then heating the mixture at an elevated temperature to effectuate in situ reaction between the wax and the alcohol, thereby resulting in a composition with the chemically modified wax formed in situ therein.

The chemically modified wax is preferably present in an amount ranging from about 0.1% to about 20% by total weight of the composition. More preferably, the chemically modified wax is present in an amount not more than 15%, e.g., from about 1% to about 10%, and most preferably from about 2% to about 6%, by total weight of the composition.

Another component of the mascara composition of the present invention is a polymeric film former comprising monomers having the formula

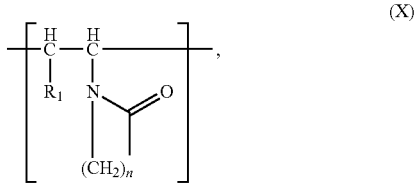

(X)

and monomers having the formula

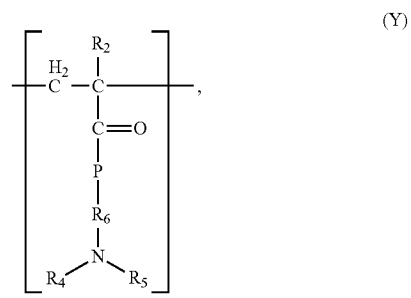

(Y)

wherein n is 3 to 6; P is O or $NR_3$; $R_1$, $R_2$, $R_3$, $R_4$, and $R_5$ are independently H or $C_1$-$C_5$ alkyl; R6 is $C_2$-$C_{16}$ alkyl or alkylene; wt % of X monomers ranges from about 60 to about 99, more preferably from about 70 to about 95, and most preferably from about 80 to about 90; wt % of Y monomers ranges from about 1 to about 40, more preferably from about 5 to about 30, and most preferably from about 10 to about 20.

Preferably, n is 3, so that the X monomer is vinylpyrrolidone. The Y monomer can be selected from the group consisting of alkylaminoalkyl methacrylamide monomers, alkylaminoalkylene methacrylamide monomers, alkylaminoalkyl methacrylate monomers, alkylaminoalkylene methacrylate monomers, alkylaminoalkyl acrylamide monomers, alkylaminoalkylene acrylamide monomers, alkylaminoalkyl acrylate monomers, and alkylaminoalkylene acrylate monomers. Correspondingly, the polymeric film former of the present invention can be selected from the group consisting of vinylpyrrolidone/alkylaminoalkyl methacrylamide copolymers, vinylpyrrolidone/alkylaminoalkylene methacrylamide copolymers, vinylpyrrolidone/alkylaminoalkyl methacrylate copolymers, vinlypyrrolidone/alkylaminoalkylene methacrylate copolymers, vinlypyrrolidone/alkylaminoalkyl acrylamide copolymers, vinlypyrrolidone/alkylaminoalkylene acrylamide copolymers, vinlypyrrolidone/alkylaminoalkyl acrylate copolymers, and vinlypyrrolidone/alkylaminoalkylene acrylate copolymers. Most preferred as the polymeric film former of the present invention is a vinylpyrrolidone/dimethylaminopropyl methacrylamide (DMAPMA) copolymer, which is commercially available under the trade name "STYLEZE® CC-10" from International Specialty Products (ISP) in Wayne, N.J.

The above-described polymeric film former is preferably present in an amount ranging from about 0.1% to about 70% by total weight of the composition. More preferably, the polymeric film former is present in an amount ranging from about 1% to about 20%, and most preferably from about 2% to about 10%, by total weight of the composition.

Although not wishing to be bound by any particular theory, it is believed by the inventors that the chemically modified wax and the specific polymeric film former of the present invention jointly form a soft, flexible mascara coating over the eyelashes that can be readily re-wetted by the aqueous phase(s) contained in a newly applied coating of mascara and thereby allow re-application of such mascara composition to the eyelashes directly over the mascara-coated eyelashes. As shown in the comparative examples hereinafter, mascara compositions containing the chemically modified wax in combination with several polymeric film formers typically used in conventional mascara compositions do not have the re-wettable characteristic of the mascara compositions of the present invention and cannot be comfortably re-applied to mascara-coated eyelashes. Therefore, selection of the specific polymeric film former and the combined use of such specific film former with the chemically modified wax by the present invention to form a re-applicable mascara composition are both surprising and un-expected over the conventional art.

The mascara compositions of the present invention typically contain one or more fillers, inorganic or organic pigments, such as iron oxides or D&C or FD&C colorants or lakes thereof. Suggested ranges of such fillers and pigments are from about 0.1 to 80%, preferably from about 0.1 to 50%. Specific examples of particulate fillers include talc, mica, magnesium carbonate, calcium carbonate, magnesium silicate, aluminum magnesium silicate, silica, polyethylene powder, methacrylate powder, polystyrene powder, silk powder, crystalline cellulose, starch, titanated mica, bismuth oxychloride, zinc oxide, and the like. Pigments include iron oxides such as red, yellow iron, black iron oxides, ultramarines, iron oxide titanated mica, salts or lakes of aluminum, barium or calcium, and the like. Other colors, such as organic or synthetic dyes, can also be included in the cosmetic compositions of the present invention.

In a preferred, but not necessary, embodiment of the present invention, the pigments are hydrophilic, which may include, but are not limited to pigments that are inherently hydrophilic (e.g., metal oxides) due to their polarity, or pigments (e.g., carbon black) that are surface-treated with a material so as to confer hydrophilicity. Pigment treatment materials that may confer hydrophilicity include silicone surfactants, such as oxyalkylenated silicones, PEG-dimethicones, dimethicone copolyol, alkyl-substituted dimethicone copolyols (e.g., cetyl or stearyl dimethicone copolyol); sulfopolyesters, such as those commercially available under the tradenames of Eastman AQ 14000 and Eastman AQ 55 from Eastman Chemical Company (Kingsport, Tenn.). The use of hydrophilic pigments functions to further improve the re-wettability of the mascara compositions of the present invention. For example, iron oxides surface-treated with PEG-9 dimethicone or decyl glucoside can be readily used in the present invention. Carbon black surface-treated with Eastman AQ 55 polymer can also be used for the practice of the present invention. The hydrophilic pigments may present in the mascara compositions of the present invention at an amount ranging from about 0.1% to about 30%, and preferably from about 0.5% to about 20%, by total weight of the compositions.

As mentioned hereinabove, the mascara composition of the present invention is aqueous-based, and it preferably contains from about 5% to about 90%, and most preferably from about 20% to about 70%, of water. In addition to water, the aqueous phase may further include a water-miscible solvent (generally having a water-miscibility of greater than 50% by weight at 25° C.). Examples of such water-miscible solvents include $C_1$-$C_5$ monoalcohols, such as ethanol or isopropanol, $C_2$-$C_8$ glycols, such as propylene glycol, ethylene glycol, butylene glycol, and dipropylene glycol, $C_3$-$C_4$ ketones and $C_2$-$C_4$ aldehydes. Such water-miscible solvent may be presented in an amount ranging from about 0.01% to about 40%, and more preferably from about 0.5% to about 10%, by total weight of the composition.

The aqueous mascara composition of the present invention can be in the form of either oil-in-water emulsion or water-in-oil emulsion with one or more lipophilic materials included therein. The lipophilic materials can be selected from oils and fats commonly used in the cosmetic products, and if present, such oils and fats are provided in a total amount ranging from about 0.1% to about 40%, more preferably from about 0.5% to about 20%, by total weight of the composition. Oils typically used in cosmetic products include polar oils, non-polar oils, volatile oils, non-volatile oils, and mixtures thereof. More specifically, the oils can be selected from the group consisting of hydrocarbon-based oils, fluoro and/or silicone oils, oils of mineral, animal, plant, or synthetic origin, provided that that they form a homogeneous and stable mixture along with other ingredients of the mascara composition of the present invention. Exemplary oils for use in the mascara compositions of the present invention include polyisobutene, polybutene, polydecene, or hydrogenated derivatives thereof. Fats as employed by the present invention may be selected from the group consisting of vegetable fats, synthetic fats, and mixtures thereof. Preferably the fats used in the present invention are $C_6$-$C_{30}$ fatty acids or $C_6$-$C_{30}$ fatty acid mono- or diesters of glycerin selected from the group consisting of glyceryl stearates, diglyceryl distearate, diglyceryl diisostearate, glyceryl palmitates, palmitates of $C_{18}$-$C_{36}$ triglyceride, glyceryl behenates, and mixtures thereof.

In addition to the chemically modified wax as described herein, the mascara composition of the present invention may include one or more additional structuring agents including other waxes commonly used in cosmetic products or other ingredients that increase the viscosity or thickness of the composition. If present, the additional structuring agents are preferably provided in a total amount ranging from about 0.1% to about 70%, and more preferably from about 0.5% to about 60%, by total weight of the composition. Examples of other waxes include, but are not limited to animal waxes, vegetable waxes, mineral waxes, various fractions of natural waxes, synthetic waxes, petroleum waxes, polyethylene waxes, polypropylene waxes, polyurethane waxes, hydrocarbon-based waxes such as Fischer-Tropsch waxes, silicone waxes, and mixtures thereof. Preferred other waxes in practice of the present invention include beeswax, lanolin wax, shellac wax, carnauba wax, candelilla wax, bayberry wax, ozokerite, ceresin, paraffin, microcrystalline waxes, polyethylene waxes, $C_{24}$-$C_{45}$ methicones, and the like. Other types of structuring agents can also be used for increasing the viscosity or thickness of the mascara compositions of the present invention, such as those having an HLB of from about 1 to about 8 and having a melting point of at least about 45° C.

Other suitable structuring agents may include saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C. Preferred other structuring agents for practice of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred other structuring agents are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

Also useful as structuring agents, particularly in the aqueous phase of the compositions of the present invention, are hydrophilic gelling agents such as the acrylic acid/ethyl acrylate copolymers and the carboxyvinyl polymers sold by the B.F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10-30 Alkyl Acrylate Crosspolymer). Combinations of the above polymers are also useful herein. Other gelling agents suitable for use herein include oleogels such as trihydroxystearin. Hydrophobically modified celluloses are also suitable for use as structuring agents. If present, the gelling agents are provided in a total amount ranging from about 0.05% to about 20%, and more preferably from about 0.5% to about 10%, by total weight of the composition.

In some embodiments, the mascara composition of the present invention may further include fibers for lash lengthening effects. The fibers useful in the present invention can be either natural fibers or synthetic fibers. Natural fibers include, but are not limited to: cotton fibers, silk fibers, wool fibers, and the like. Synthetic fibers include, but are not limited to: polyester fibers, rayon fibers, nylon fibers, and other polyamide fibers. If present, the fibers are preferably provided at an amount ranging from about 0.01% to about 10% by total weight of the composition.

The mascara composition of the present invention may also contain one or more hair care actives, such as hair straightening agents, hair curling agents, hair conditioning agents, hair growth agents, and the like. If present, such hair care actives may range from about 0.01% to about 50%, preferably from about 0.05% to about 35% by total weight of the composition.

The cosmetic composition of the present invention may further include one or more humectants. If present, they may range from about 0.1 to 20% by weight of the total composition and include polyhydric alcohols including glycerol, $C_{1-4}$ alkylene glycols such as butylene, propylene, ethylene glycol, glycerin, and the like, polyalkylene glycols, and alkylene polyols and mixtures thereof, hyaluronic acid, urea, sorbitol, sodium 2-pyrrolidone-5-carboxylate, soluble collagen, dibutylphthalate and gelatin.

A variety of water soluble preservatives can be added to the cosmetic compositions of the present invention to provide a prolonged shelf life. Suitable preservatives include, but are not limited to: potassium sorbate, imidazolidinyl urea, p-hydroxy benzoate, esters of p-hydroxybenzoic acid, various parabens (as disclosed in the 12$^{th}$ Edition of CTFA's International Cosmetic Ingredient Dictionary and Handbook), ethylhexylglycerin, caprylyl glycol/phenoxyethanol/hexylene glycol, and the like. Other preservatives suitable for use in the cosmetic compositions of the present invention are disclosed in the 12$^{th}$ Edition of CTFA's International Cosmetic Ingredient Dictionary and Handbook, the entire disclosure of which is herein incorporated by reference for all purposes.

The cosmetic composition of the present invention may optionally comprise a fragrance in an amount sufficient to make the composition more appealing to the consumer. Preferably, the fragrance is in the amount of from about 0.001% to about 10% by total weight of the composition.

The mascara compositions of the present application can be first applied to the eyelashes to form an initial coating thereover, and it can be readily re-applied to mascara-coated eyelashes to form one or more additional coatings over the eyelashes after the initial coating is allowed to dry for a sufficient period of time. Such sufficient period of time can range from about 10 seconds to about 2 minutes. Further, the mascara compositions of the present application can be re-applied to mascara-coated eyelashes after an extended period of time, e.g., more than 10 minutes or more preferably, more than 1 hour after application of the initial coating. Most advantageously, the mascara compositions of the present application can be re-applied as many times as desired to form multiple additional coatings, each of which is allowed to dry for a sufficient period of time and each is directly applied over the previous coating, so as to continuously build up the lash volume for a desired dramatic effect.

The following examples further illustrate various specific embodiments of the present invention, without limiting the broad scope thereof.

EXAMPLE 1

Mascara Composition

| Formula 1 | |
|---|---|
| Components | Wt % |
| Deionized Water | 56.39 |
| Hydroxyethylcellulose | 0.50 |
| Aminomethyl propanediol | 1.58 |
| Butylene glycol | 1.00 |
| Disodium EDTA | 0.10 |
| Iron oxide/PEG-9 dimethicone | 2.50 |
| Water/D&C Black #2 Dye/*Acacia Senegal* gum/decyl glucoside | 5.00 |
| Simethicone | 0.08 |
| Mica | 4.00 |
| Vinylpyrrolidone/DMAPMA copolymer | 5.00 |
| Stearic acid | 6.10 |
| Paraffin wax | 3.20 |
| PEG-8 beeswax | 4.00 |
| Carnauba wax | 1.60 |
| Glyceryl stearate | 5.00 |
| Polyisobutene | 1.60 |
| Phenoxyethanol/caprylyl glycol/potassium sorbate/water/hexylene glycol | 0.70 |
| Ethylhexylglycerin | 0.60 |
| Green tea extract | 1.00 |
| Water/polyaminopropyl biguanide | 0.05 |

EXAMPLE 2

Comparative Study

A comparative study was carried out in order to evaluate the compatibility of polymeric film formers other than the VP/DMAPMA copolymer with the PEG-8 beeswax in forming re-applicable mascara compositions. Specifically, Comparative Formulas 2-5, which contained all the ingredients of Formula 1 except that the VP/DMAPMA copolymer therein was replaced with other polymers, were formed, as follows:

| Comparative Formulas 2-5 | | | | |
|---|---|---|---|---|
| | Wt % | | | |
| Components | Formula 2 | Formula 3 | Formula 4 | Formula 5 |
| Deionized Water | 56.39 | 56.39 | 56.39 | 56.39 |
| Hydroxyethylcellulose | 0.50 | 0.50 | 0.50 | 0.50 |
| Aminomethyl propanediol | 1.58 | 1.58 | 1.58 | 1.58 |
| Butylene glycol | 1.00 | 1.00 | 1.00 | 1.00 |
| Disodium EDTA | 0.10 | 0.10 | 0.10 | 0.10 |
| Iron oxide/PEG-9 dimethicone | 2.50 | 2.50 | 2.50 | 2.50 |
| Water/D&C Black #2 Dye/*Acacia Senegal* gum/decyl glucoside | 5.00 | 5.00 | 5.00 | 5.00 |
| Simethicone | 0.08 | 0.08 | 0.08 | 0.08 |
| Mica | 4.00 | 4.00 | 4.00 | 4.00 |
| Vinylpyrrolidone/DMAPMA copolymer | — | — | — | — |
| DAITOSOL 5000J (water/acrylates/octyl acrylate copolymer) | 5.00 | — | — | — |
| SYNTRAN EX35-1 (ammonium acrylates copolymer/butylene glycol/sodium laureth-12 sulfate) | — | 5.00 | — | — |
| COVACRYL P12 (water/acrylate copolymer) | — | — | 5.00 | — |
| THORCO FLEX IV C (water/ polyvinyl acetate/acrylates/ hydroxyesters acrylates copolymer/butylene glycol) | — | — | — | 5.00 |
| Stearic acid | 6.10 | 6.10 | 6.10 | 6.10 |
| Paraffin wax | 3.20 | 3.20 | 3.20 | 3.20 |
| PEG-8 beeswax | 4.00 | 4.00 | 4.00 | 4.00 |
| Carnauba wax | 1.60 | 1.60 | 1.60 | 1.60 |
| Glyceryl stearate | 5.00 | 5.00 | 5.00 | 5.00 |
| Polyisobutene | 1.60 | 1.60 | 1.60 | 1.60 |
| Phenoxyethanol/caprylyl glycol/ potassium sorbate/water/ hexylene glycol | 0.70 | 0.70 | 0.70 | 0.70 |
| Ethylhexylglycerin | 0.60 | 0.60 | 0.60 | 0.60 |
| Green tea extract | 1.00 | 1.00 | 1.00 | 1.00 |
| Water/polyaminopropyl biguanide | 0.05 | 0.05 | 0.05 | 0.05 |

When applied to eyelashes, Formula 1 formed a flexible coating that could be easily re-wetted and re-applied after 3 hours of the initial application, with minimum difficulty of application and little clumping. In contrast, all of the Comparative Formulas 2-5 formed rigid coatings that could not be re-wetted by the respective comparative mascara formula, and re-application of the comparative mascara composition over already-coated lashes was difficult. Therefore, it was demonstrated that selection of the specific polymeric film former and the combined use of such specific film former with the chemically modified wax by the present invention to form a re-applicable mascara composition are both surprising and un-expected over the conventional art.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A mascara composition comprising:
   (a) a chemically modified wax with one or more hydrophilic functional groups;
   (b) a polymeric film former comprising monomers having the formula

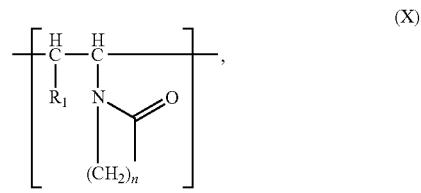

(X)

and monomers having the formula

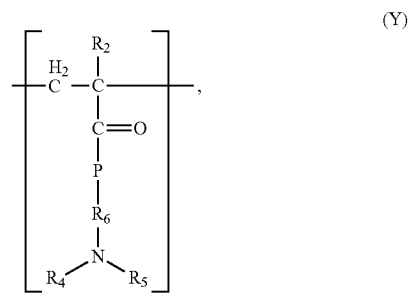

(Y)

wherein n is 3 to 6; P is O or $NR_3$; $R_1$, $R_2$, $R_3$, $R_4$, and $R_5$ are independently H or $C_1$-$C_5$ alkyl; $R_6$ is $C_2$-$C_{16}$ alkyl or alkylene; wt % of X monomers ranges from about 60 to about 99; and wt % of Y monomers ranges from about 1 to about 40;
   (c) pigments; and
   (d) water.

2. The mascara composition of claim 1, wherein the chemically modified wax is formed by reacting a synthetic or natural wax with a mono-, di-, or polyhydric or alkoxylated alcohol.

3. The mascara composition of claim 1, wherein chemically modified wax is formed by reacting a natural wax with polyethylene glycol (PEG).

4. The mascara composition of claim 3, wherein the chemically modified is selected from the group consisting of PEG-esterified beeswax, PEG-esterified candelilla wax, PEG-esterified carnauba wax, PEG-esterified lanolin, PEG-esterified spermaceti wax, PEG-esterified shellac wax, PEG-esterified bayberry wax, and PEG-esterified sugar cane wax.

5. The mascara composition of claim 1, wherein the chemically modified wax is selected from the group consisting of PEG-8 beeswax, PEG-6 beeswax, PEG-12 beeswax, PEG-12 carnauba wax, and PEG-sorbitan beeswax.

6. The mascara composition of claim 1, wherein the chemically modified wax is present in an amount ranging from about 0.1% to about 20% by total weight of the composition.

7. The mascara composition of claim 1, wherein the chemically modified wax is present in an amount ranging from about 1% to about 10% by total weight of the composition.

8. The mascara composition of claim 1, wherein the polymeric film former is selected from the group consisting of vinylpyrrolidone/alkylaminoalkyl methacrylamide copolymers, vinylpyrrolidone/alkylaminoalkylene methacrylamide copolymers, vinlypyrrolidone/alkylaminoalkyl methacrylate copolymers, vinlypyrrolidone/alkylaminoalkylene methacrylate copolymers, vinlypyrrolidone/alkylaminoalkyl acrylamide copolymers, vinlypyrrolidone/alkylaminoalkylene acrylamide copolymers, vinlypyrrolidone/alkylaminoalkyl acrylate copolymers, and vinylpyrrolidone/alkylaminoalkylene acrylate copolymers.

9. The mascara composition of claim 1, wherein the polymeric film former is a vinylpyrrolidone/dimethylaminopropyl methacrylamide (DMAPMA) copolymer.

10. The mascara composition of claim 1, wherein the polymeric film former is present in an amount ranging from about 0.1% to about 20% by total weight of the composition.

11. The mascara composition of claim 1, wherein the polymeric film former is present in an amount ranging from about 1% to about 10% by total weight of the composition.

12. The mascara composition of claim 1, wherein the pigments are hydrophilic pigments.

13. The mascara composition of claim 12, wherein the hydrophilic pigments comprises pigments surface-treated with a hydrophilic material.

14. The mascara composition of claim 1, wherein the pigments are present in a total amount ranging from about 1% to about 30% by total weight of the composition.

15. The mascara composition of claim 1, wherein water is present in an amount ranging from about 20% to about 90% by total weight of the composition.

16. The mascara composition of claim 1, wherein water is present in an amount ranging from about 40% to about 70% by total weight of the composition.

17. The mascara composition of claim 1, wherein said composition is in the form of an oil-in-water emulsion.

18. A method of enhancing the appearance of eyelashes comprising applying a first coating of a mascara composition according to claim 1 over the eyelashes, and subsequently applying one or more additional coatings of said mascara composition over the eyelashes after the first coating is allowed to dry thereon for a sufficient period of time.

19. The method of claim 18, wherein the first coating is allowed to dry for at least 10 minutes before application of the additional coatings.

20. The method of claim 18, wherein the subsequent application of additional coatings is carrier out more than 1 hour after application of the first coating.

21. The method of claim 19, wherein two or more additional coatings are subsequently applied to the eyelashes, and wherein each additional coating is allowed to dry for a sufficient period of time before application of the next coating.

* * * * *